United States Patent
Escalante et al.

(10) Patent No.: US 6,262,314 B1
(45) Date of Patent: Jul. 17, 2001

(54) PROCESS FOR PREPARATION OF ETHERS IN A CATALYTIC DISTILLATION COLUMN

(75) Inventors: Leonardo Escalante; Jose Castor Gonzalez, both of San Antonio de los Altos; Zaida Hernandez, Estado Miranda, all of (VE)

(73) Assignee: Intevep, S.A., Caracas (VE)

( * ) Notice: Subject to any disclaimer, the term of this patent is extended or adjusted under 35 U.S.C. 154(b) by 0 days.

(21) Appl. No.: 09/286,722

(22) Filed: Apr. 6, 1999

(51) Int. Cl.⁷ .............................. C07C 41/01; B01D 3/34
(52) U.S. Cl. ..................... 568/697; 203/38; 203/DIG. 6
(58) Field of Search .............................. 568/697; 203/38, 203/DIG. 6, 28, 29

(56) References Cited

U.S. PATENT DOCUMENTS

| | | | |
|---|---|---|---|
| 4,950,803 | * 8/1990 | Smith, Jr. et al. | 568/697 |
| 5,248,837 | * 9/1993 | Smith, Jr. et al. | 568/697 |
| 5,313,005 | 5/1994 | Smith, Jr. et al. | 568/697 |
| 5,382,706 | * 1/1995 | Gonzalez et al. | 568/697 |
| 5,420,360 | 5/1995 | Chin et al. . | |
| 5,431,888 | 7/1995 | Hickey et al. | 422/191 |
| 5,536,886 | 7/1996 | Tamminen et al. | 568/697 |
| 5,689,012 | 11/1997 | Jarvelin et al. | 568/697 |

FOREIGN PATENT DOCUMENTS 0 885 866   12/1998  (EP) .

* cited by examiner

Primary Examiner—Johann Richter
(74) Attorney, Agent, or Firm—Bachman & LaPointe, P.C.

(57) ABSTRACT

A process for preparing ethers includes the steps of:

providing a feedstock containing iso-olefins selected from the group consisting of C5 iso-olefins, C6 iso-olefins and mixtures thereof; mixing the feedstock with alkyl alcohol so as to provide a reaction feedstock, feeding the reaction feedstock to a reactor zone in the presence of a first etherification catalyst whereby the alkyl alcohol reacts with the iso-olefins to form alkyl-tert-alkyl ethers so as to provide an intermediate feedstock containing the ethers and unreacted iso-olefins and alkyl alcohol; feeding the intermediate feedstock to a catalytic distillation column having a second etherification catalyst defining a catalytic zone; mixing additional alkyl alcohol to the intermediate feedstock so as to form azeotropes of the alkyl alcohol with the unreacted iso-olefins without forming azeotropes of the alkyl alcohol with the ethers whereby the catalytic zone is substantially free of the ethers and the unreacted iso-olefins react with said alkyl alcohol in the catalytic zone to form additional alkyl-tert-alkyl ethers.

16 Claims, 1 Drawing Sheet

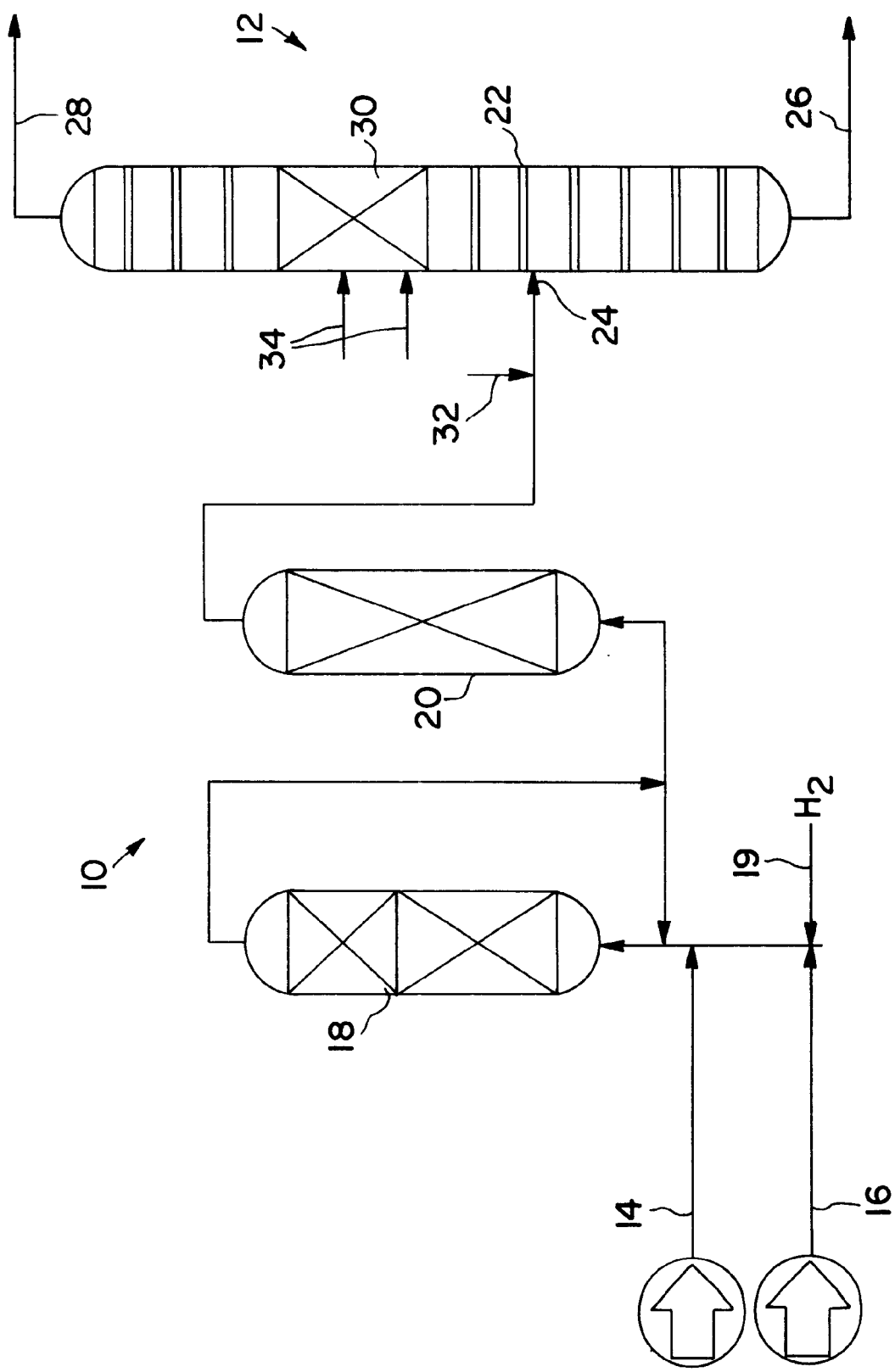

PROCESS FOR PREPARATION OF ETHERS IN A CATALYTIC DISTILLATION COLUMN

BACKGROUND OF THE INVENTION

The invention relates to a process for preparing ethers such as tert-amyl-methyl-ether (TAME) and methyl-tert-hexyl-ether (MTHE). More specifically, the invention relates to a process using etherification reactors and catalytic distillation so as to provide excellent conversion rates from C5 and C6 iso-olefins to TAME and MTHE.

Various processes are known for using catalytic distillation in order to convert iso-olefins to ethers. Examples of such methods include U.S. Pat. No. 5,431,888 to Hickey et al., U.S. Pat. No. 5,536,886 to Tamminen et al., U.S. Pat. No. 5,313,005 to Smith, Jr. et al. and U.S. Pat. No. 5,689,013 to Jarvelin et al.

In conventional processes, it is difficult to obtain conversion of both iso-C5 and iso-C6 together. In addition, conventional processes provide some conversion, but higher conversion rates are desirable.

It is therefore the primary object of the present invention to provide a process whereby excellent conversion rates of iso-olefins to ethers are achieved.

It is a further object of the present invention to provide a process wherein C5 and C6 iso-olefins are simultaneously converted to TAME and MTHE, each with excellent conversion rates.

It is a still further object of the present invention to provide a process wherein advantages of both fixed bed etherification reactors and catalytic distillation are combined to provide excellent results.

Other object and advantages of the present invention will appear hereinbelow.

SUMMARY OF THE INVENTION

In accordance with the present invention, the foregoing objects and advantages have been readily attained.

According to the invention, a process is provided for preparing ethers, which process comprises the steps of providing a feedstock containing iso-olefins selected from the group consisting of C5 iso-olefins, C6 iso-olefins and mixtures thereof; mixing said feedstock with alkyl alcohol so as to provide a reaction feedstock, feeding said reaction feedstock to a reactor zone in the presence of a first etherification catalyst whereby said alkyl alcohol reacts with said iso-olefins to form alkyl-tert-alkyl ethers so as to provide an intermediate feedstock containing said ethers and unreacted iso-olefins and alkyl alcohol; feeding said intermediate feedstock to a catalytic distillation column having of a second etherification catalyst defining a catalytic zone; mixing additional alkyl alcohol to said intermediate feedstock so as to form azeotropes of said alkyl alcohol with said unreacted iso-olefins without forming azeotropes of said alkyl alcohol with said ethers whereby said catalytic zone is substantially free of said ethers and said unreacted iso-olefins react with said alkyl alcohol in said catalytic zone to form additional alkyl-tert-alkyl ethers.

In accordance with the present invention, the feedstock may preferably contain both C5 and C6 iso-olefins which are converted respectively to TAME and MTHE.

BRIEF DESCRIPTION OF THE DRAWING

A detailed description of the preferred embodiments of the present invention follows, with reference to the attached figure which is a schematic representation of one embodiment of a process of the present invention.

DETAILED DESCRIPTION

The invention relates to a process for production of ethers, particularly heavy ethers such as tert-amyl-methyl-ether (TAME) and methyl-tert-hexyl-ether (MTHE), wherein the advantages of fixed bed etherification reactors and catalytic distillation are combined so as to provide excellent conversion rates of both C5 and C6 iso-olefins.

The feedstock for the process of the present invention preferably includes tertiary C5 or C6 iso-olefins, preferably both C5 and C6 iso-olefins. Such olefins are available in oil refinery streams such as light naphtha from fluid catalytic cracking (FCC), delayed coker or steam cracking processes. Samples of typical feedstocks are set forth in the example appended hereinbelow.

Referring to the FIGURE, a schematic representation of one embodiment of the process of the present invention is provided. In this process, reaction is carried out first in a fixed bed etherification reactor zone 10 and then in a distillation column zone 12. Feedstock 14 and an alkyl alcohol 16 are mixed to form a reaction feedstock and fed to reactor zone 10, for example as illustrated.

In accordance with the process of the present invention, alkyl alcohol and feedstock are reacted first in reactor zone 10 and then in distillation column zone 12 so as to react C5 iso-olefins, or isoamylenes (2-methyl-1-butene and 2-methyl-2-butene) with methanol to produce tertiary-amyl-methyl-ether (TAME), and also to react C6 iso-olefins (2-methyl-1-pentene, 2-methyl-2-pentene, 3-methyl-2-pentene cis and trans, 2-ethyl-1-butene, 2,3-dimethyl-1-butene, 2,3-dimethyl-2-butene and 1-methyl-1-cyclopentane) with methanol to produce four different isomer ethers that are identified as a group as methyl-tertiary-hexyl-ether (MTHE). These four isomers specifically are 2-methyl-2-methoxy-pentane, 3-methyl-3-methoxy-pentane, 2,3-dimethyl-2-methoxy-pentane and 1-methyl-1-methoxy-cyclopentane. These reactions are desirable, and excellent conversion rates are advantageously provided in accordance with the present invention, so as to provide the desired ethers which are useful as blending components for gasoline, and/or as fuels in their own right.

Feedstock 14 and alkyl alcohol 16 are preferably fed to reactor zone 10 at a molar ratio of alkyl alcohol to iso-olefins in the feed of between about 1.05 and about 1.6. This is desirable so as to insure a stoichiometric excess of alkyl alcohol for the etherification reaction, while avoiding too much excess alkyl alcohol which can promote the dimerization of iso-olefins and formation of undesired by-products such as dimethyl ether.

Reactor zone 10 may suitably be any conventional catalytic etherification fixed bed reactor, and may preferably be provided as a first reactor 18 and second reactor 20 connected serially for sequentially treating feedstock. Reactors are shown in FIG. 1 as up-flow reactors, and it is preferred that a suitable etherification catalyst be disposed in each reactor. Other configurations may be used within the scope of the invention.

Suitable etherification catalysts include conventional porous strongly acidic ion exchange resins such as K2631 resin provided by Bayer, and A-15 and A-35 resins provided by Rohm and Haas.

In cases where the feed contains appreciable portions of diolefins, it is preferred that first reactor 18 be provided with an etherification catalyst that is doped with a small amount of noble metal such as palladium, which metal serves to promote hydrogenation of the diolefin fractions to olefins, as well as some double bond isomerization of olefins. This is desirable so as to reduce the potential for fouling of the catalyst from diolefins, and also to increase to some extent the amount of reactive olefins which can be converted to ethers in accordance with the present invention. If diolefin conversion is desired in first reactor 18, a stream 19 of hydrogen to first reactor 18 is also desirable. This embodiment of the invention is further discussed below.

Suitable reaction alkyl alcohol to be added in accordance with this process is methanol for the production of TAME and MTHE. Other alkyl alcohols could be used as appropriate, if it is desirable to produce other ethers.

The desired etherification reactions are all exothermic and take place in the liquid phase at moderate temperatures and pressures. Thus, reactors 18, 20 may suitably be operated at pressures of between about 1 barg and about 30 barg, preferably about 10 barg, and at temperatures between about 50° C. and about 95° C., preferably between about 70° C. and about 85° C. in first reactor 18 and about 65° C. in second reactor 20.

The liquid phase etherification reaction carried out in zones 18, 20 is thermodynamically limited, and conversion approaching equilibrium is typically obtained at the outlet of second reactor 20. Thus, the partially treated intermediate feedstock exiting second reactor 20 will typically exhibit a conversion of C5 iso-olefins to TAME of at least about 50% (wt.), and preferably between about 65% and about 70%, and a conversion of C6 iso-olefins to MTHE of at least about 25% (wt.) and preferably between about 30% and about 40%. The remainder of the intermediate feedstock will include unreacted C5 and C6 iso-olefins and remaining methanol, as well as other unreactive elements contained in the original feedstock. The distillation column zone 12 operated according to the present invention advantageously provides additional conversion of unreacted C5 iso-olefins to TAME of at least about 10% (wt.), and additional conversion of unreacted C6 iso-olefins to MTHE of at least about 20% (wt.) This intermediate feedstock is then fed to distillation column zone 12 where, in accordance with the present invention, already produced ethers are carefully separated from the unreacted iso-olefins and alkyl alcohol which, in the presence of an additional etherification catalyst, results in further conversion of the unreacted iso-olefins to additional TAME and MTHE. By carefully separating and maintaining the catalyst zone free of produced ethers, excellent total conversion rates can be obtained.

As shown in FIG. 1, distillation column zone 12 may suitably include a distillation column 22 having an inlet 24 and an outlet 26 for bottoms and an outlet 28 for vapors and the like. Column 22 also preferably is provided with an etherification catalyst which may suitably be in the form of a catalytic packing structure that contains the catalytic material inside a permeable surface. Typical catalytic packing material, commonly referred to as "bales", preferably also includes catalytic material as a strongly acidic macroporous resin such as A-35 manufactured by Rohm and Haas. This catalytic packing is preferably provided in column 22 at a zone 30 where liquid phase reactants will be arranged to promote the additional and desired etherification reactions. The remainder of column 22 may suitably be packed with a non-catalytic random or structured packing such as those provided by Solzer, Koch, Jaeger, Glitsch and Norton. Trays can also be used in the non-catalytic section instead of packing for instance sieve trays, valve 11, and bubble caps 11 could be used.

It may also be desired to provide distillation column zone 12 as two distinct columns. In this configuration, intermediate feedstock from reactor 20 would be fed initially to a column which is packed with non-catalytic packing, and then to a column which includes the catalytic packing and a catalytic zone. As with the embodiment of the Figure, feed of intermediate feedstock and additional methanol as well as distillation column operating conditions are manipulated in accordance with the present invention so as to operate the catalytic zone without appreciable amounts of ethers being present. As set forth above, this is accomplished by monitoring the ratio of alkyl alcohol to intermediate feedstock such that sufficient alkyl alcohol is present to form azeotropes with C5 and C6 iso-olefins in the feed, without forming azeotropes with the produced ethers. This advantageously allows for the iso-olefin/alkyl alcohol azeotropes to boil up into the catalytic zone where additional reactions take place, while produced ethers exit distillation column zone 12.

In accordance with the present invention, it is critical to control the ratio of alkyl alcohol to unreacted iso-olefins in distillation column 22 such that alkyl alcohol forms azeotropes with only the C5 and C6 hydrocarbons, and not with the already produced ethers. This advantageously maintains catalytic zone 30 free of ethers. As set forth above, the etherification reaction is a thermodynamically limited reaction, and ether in the catalytic zone 30 can therefore undesirably limit further etherification reactions and, in extreme cases, could cause reverse reactions from ethers back to iso-olefins.

In order to maintain the appropriate amounts of alkyl alcohol in distillation column 22, additional alkyl alcohol can be mixed either directly with intermediate feedstock 24 as illustrated at 32, or may be fed directly to catalytic zone 30 as illustrated at 34. Of course, additional alkyl alcohol could be introduced at other locations as well.

By carefully monitoring conditions and ratios of products in distillation column 22, excellent additional rates of conversion of both C5 and C6 iso-olefins to TAME and MTHE respectively can be accomplished. It is preferred that operating conditions in the distillation column be maintained as set out in Table 1 below:

TABLE 1

Pressure=20–60 psig (1.5–4.0 barg),(top)
Reboiler Temperature=120–170° C.
Reflux Ratio=0.7–2.5 vol/vol
Methanol/Iso-olefins Ratio (Column Inlet)=2.5–6.0 mol/mol
Catalytic Section Temperature=60–90° C.
Methanol Content in the Liquid Phase of Catalytic Section=15–50 wt. %

By maintaining the aforesaid conditions at distillation column 22, total conversion of reactive C5 iso-olefin to TAME can be provided at values of at least about 70% (wt.), preferably at least about 80% (wt.), and total conversion of C6 iso-olefins to MTHE can be obtained of at least about 55% (wt.), preferably at least about 65% (wt.).

Outlet 26 of column 22 when operated in accordance with the process of the present invention can provide a product stream containing 90% or more of converted ethers, while the top stream from outlet 28 typically contains the inert compounds, excess methanol and a very small amount of unreacted but reactive iso-olefins.

As set forth above, it may be desired to provide a hydrogen stream 19 as feed to reactor 18 for reaction with noble-metal doped catalyst in reactor zone 10. This advantageously serves to remove unwanted diolefins which would otherwise foul the catalyst in reactor zone 10.

It has also been found that the previous history or startup procedure of the column affects the internal conditions in such a way that undesired azeotropes may be formed even keeping the feed and the operating conditions within the desired range. This means that several steady states may be achieved depending on the way the column was operated previously. For instance, if the column has high internal concentrations of methanol, due to previous operating conditions, then it is very likely that the undesired TAME-MeOH azeotropes will form leading to very low conversions of isoamylenes to TAME, even with a feed that has a reduced amount of methanol and under operating conditions that in other situations will give high conversions to ethers. This becomes obvious if the column is started up fully loaded with methanol. If the mixture of methanol-hydrocarbons is then introduced in the column, the formation of undesired azeotropes is practically unavoidable. On the other hand, if the column is started up free of methanol, the formation of azeotropes will mainly depend on the feed composition (ratio methanol/hydrocarbons) and on the operating conditions.

The following example demonstrates the importance of certain process parameters in accordance with the process of the present invention.

EXAMPLE

In this example, a pilot plant was used having a configuration substantially similar to that set forth in the Figure. The first fixed bed reactor was loaded with 250 cc (92.5 g) of strongly acidic macroporous resin doped with 3 g/l of palladium. This is a catalyst provided by Bayer and referred to as K2634. This doped resin was provided in the bottom portion of the reactor, while the top portion of the first reactor was loaded with 125 cc (46.25 g) of strongly acidic macroporous resin without palladium, which is a catalyst provided by Bayer and identified as K2631. The second fixed bed reactor contained 375 cc (138.7 g) of the same non-doped catalyst K2631. In the distillation column zone, two columns were provided, each having a diameter of 2.54 cm and height of 8 m. The first column was loaded with a non-catalytic random packing (4 mm Propack, provided by Scientific Development Co.). In the second column, the bottom six meters of height were loaded with a catalytic distillation packing which contained 329g of strongly acidic macroporous resin (A-35 manufactured by Rohm Haas), while the top two meters of this second column were loaded with the same 4 mm Propack non-catalytic packing.

The feedstock used was a C5/C6 cut obtained from a light catalytic cracking naphtha (LCCN) produced from a fluid catalytic cracking unit. Table 2 set forth below contains description of the composition of three separate feedstocks used for three separate operations in this example. The feedstock was mixed with methanol, which had a purity of 99.9% weight, and hydrogen (purity 99.9%) was fed to the feedstock at the inlet to the first reactor.

TABLE 2

|  |  | Run 1 | Run 2 | Run 3 |
|---|---|---|---|---|
| Non-Reactive C4's | (wt. %) | 9.96 | 12.90 | 13.98 |
| Non-Reactive C5's | (wt. %) | 31.35 | 32.26 | 30.82 |
| 2-Methyl-Butene-1 | (wt. %) | 5.05 | 5.00 | 5.15 |

TABLE 2-continued

|  |  | Run 1 | Run 2 | Run 3 |
|---|---|---|---|---|
| 2-Methyl-Butene-2 | (wt. %) | 9.75 | 9.42 | 5.27 |
| 3-Methyl-Butene-1 | (wt. %) | 0.89 | 0.94 | 1.51 |
| Non-Reactive C6's | (wt. %) | 32.96 | 27.78 | 28.63 |
| 4-Methyl/3-Methyl-Pentene-1 | (wt. %) | 1.07 | 1.03 | 1.05 |
| 2,3-Di-Methyl-Butene-1 | (wt. %) | 0.67 | 0.64 | 0.65 |
| 4-Methyl-Cis-Pentene-2 | (wt. %) | 0.37 | 0.37 | 0.37 |
| 4-Methyl-Trans-Pentene-2 | (wt. %) | 1.14 | 1.12 | 1.19 |
| 2-Methyl-Pentene-1 | (wt. %) | 1.86 | 1.92 | 1.81 |
| 2-Ethyl-Butene-1 | (wt. %) | 0.52 | 0.58 | 0.52 |
| 2-Methyl-Pentene-2 | (wt. %) | 2.18 | 2.33 | 2.45 |
| 3-Methyl-Cis-Pentene-2 | (wt. %) | 1.35 | 1.43 | 1.60 |
| 3-Methyl-Trans-Pentene-2 | (wt. %) | 1.32 | 1.37 | 2.08 |
| 1-Methy-Cyclo-Pentene | (wt. %) | 0.23 | 0.25 | 1.63 |
| C7 plus | (wt. %) | 0.65 | 0.66 | 1.29 |
| Total reactive C5 iso-olefins | (wt. %) | 15.69 | 15.36 | 11.93 |
| Total reactive C6 iso-olefins | (wt. %) | 9.39 | 11.04 | 13.35 |

In general, the effluent from the second reactor was mixed with secondary methanol as desired so as to provide the intermediate reaction feedstock which was fed to the middle section of the first column. In this first column, ethers formed in the initial reactor zone or in the second distillation column are separated into a bottom stream, which exits to a reboiler. This stream also contains small amounts of methanol and unreacted hydrocarbons.

Vapors exiting the top of the first column are fed directly to the bottom of the second column, where they contact the catalytic packing and the desired etherification reactions take place. Liquid coming from the bottom of the second column is circulated to the top of the first column for further distillation. Vapors from the top of the second column contain mainly unreacted C5 and C6 hydrocarbons and methanol, and these vapors are condensed, a fraction is recycled back to the top of the second column as reflux, and the remainder is obtained as a top product.

Adiabatic behavior of the second column was maintained by using electric furnaces associated with the second column which were controlled to insure that the net heat transfer between the column and the environment was zero.

The main operating conditions for the pilot plant for three different runs, as well as the results obtained for these runs, are set forth in Table 3 below.

TABLE 3

|  |  | Run 1 | Run 2 | Run 3 |
|---|---|---|---|---|
| Pressure in the fixed bed reactors | (barg) | 20.0 | 20.0 | 20.0 |
| Pressure in the distillation columns | (barg) | 2.1 | 1.7 | 3.5 |
| Avg. temperature 1st fixed bed reactor | (° C.) | 76.2 | 76.8 | 80.9 |
| Avg. temperature 2nd fixed bed reactor | (° C.) | 63.5 | 63.1 | — |
| Second Column Catalyst Temperature | (° C.) | 82.8 | 82.8 | 95.1 |
| First Column Bottom Temperature | (° C.) | 140.4 | 121.8 | 165.2 |
| Flow of C5/C6 feed stream | (gr/hr) | 270.3 | 307.1 | 414.5 |
| Flow of Primary Methanol | (gr/hr) | 53.3 | 78.2 | 110.7 |
| Flow of Secondary Methanol | (gr/hr) | 26.1 | 0.0 | 0.0 |
| Ratio Methanol/(C4 + C5 + C6) to Column | (wt/wt) | 0.14 | 0.16 | 0.32 |
| Ratio Methanol/Iso-olefins to Column | (mol/mol) | 5.3 | 2.8 | 3.7 |
| Methanol Content in the Column Feed | (wt. %) | 9.3 | 10.6 | 21.1 |

TABLE 3-continued

|  |  | Run 1 | Run 2 | Run 3 |
|---|---|---|---|---|
| Methanol Content in the Column Top Product | (wt. %) | 17.9 | 18.0 | 18.1 |
| Methanol Content in Liquid from Bottom of the Catalytic Section of the Second Column | (wt. %) | 26.0 | 32.8 | 50.1 |
| TAME Content in Liquid from Bottom of the Catalytic Section of the Second Column | (wt. %) | 1.0 | 7.6 | 12.3 |
| MTHE Content in Liquid from Bottom of the Catalytic Section of the Second Column | (wt. %) | 0.0 | 1.5 | 1.9 |
| Isoamylenes Conversion (TAME Yields) | | | | |
| Primary Fixed Bed Reactors | (%) | 80.0 | 71.2 | 44.0 |
| Catalytic Distillation Section | (%) | 28.3 | -20.2 | -13.8 |
| Overall | (%) | 85.7 | 65.4 | 36.0 |
| C6 Iso-Olefins Conversion (MTHE Yields) | | | | |
| Primary Fixed Bed Reactors | (%) | 38.5 | 35.6 | 23.9 |
| Catalytic Distillation Section | (%) | 55.5 | 33.8 | 30.1 |
| Overall | (%) | 70.6 | 57.4 | 46.8 |

Run 1 represents a process carried out in accordance with the present invention. In this run, the catalytic columns were started in a proper way, such that all additional methanol was drained from the columns. The amount of the methanol in the feed was controlled very carefully in order to keep its concentration high enough to lift the C5 and C6 compounds so as to favor etherification reactions, while avoiding formation of azeotropes with ether that would then encourage presence of such ethers in the catalytic zone of the column.

The concentration of TAME in the catalytic zone of the distillation column under these conditions was 1% (wt.), and no MTHE was present. Under these conditions, as set forth in Table 3, the catalytic distillation column provided an additional 28% conversion of remaining isoamylenes to TAME, and a 55% conversion of remaining C6 iso-olefins to MTHE. This boosted the total overall conversion of olefins to TAME and MTHE, respectively, to 86% and 71%. This is an excellent result as compared to conventional processes.

In Run 2, the process was started with the columns fully loaded with methanol. The methanol content in the feed was very similar to Run 1, as was the ratio of methanol to C5 and C6 hydrocarbons. The column was operated continuously under constant conditions similar to those of Example 1 until it was evident that a steady state had been reached. The steady state results showed that a high concentration of TAME was present in the catalytic zone of the distillation columns (7.6% (wt.)), and a moderate concentration of MTHE (1.5% (wt.)). These high concentrations of ethers in the catalytic zone inhibited the reaction progress, since this reaction tends toward thermodynamic equilibrium, and for this reason the additional conversion rates in the distillation column were very low. In fact, a negative 20% conversion of C5 isoamylenes was indicated, thereby showing that TAME was actually being decomposed into isoamylenes in the catalytic zone in the distillation columns. This rendered a total process conversion of iso-olefins of 64% TAME and 57% MTHE, which is markedly reduced as compared to the results provided according to the process of the present invention using Run 1.

These poor results were caused because it was impossible to prevent the formation of the ether-methanol azeotropes, which are undesirable, which azeotrope remained present in the catalytic section of the column and reversed the desired etherification reaction.

In Run 3, the feed to the distillation columns was carried out while mixing additional methanol so as to provide approximately twice the concentration of methanol as was present in Runs 1 and 2. The columns were started properly, that is, all methanol was drained before introducing the feedstock.

Due to the high concentration of methanol, azeotropes with ethers were formed and a 12.3% (wt.) concentration of TAME and a 2.0% (wt.) concentration of MTHE were present in the catalytic zone. For this reason, the reactions at the catalytic zone were actually decomposing TAME back to isoamylenes, at a conversion rate of −14%, which reduced the overall yield to TAME to only 36%. Thus, it is critical to maintain the content of methanol within the operating conditions of the process of the present invention.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

We claim:

1. A process for preparing ethers, comprising the steps of:
providing a feedstock containing iso-olefins selected from the group consisting of C5 iso-olefins, C6 iso-olefins and mixtures thereof,;
mixing said feedstock with alkyl alcohol so as to provide a reaction feedstock,
feeding said reaction feedstock to a reactor zone in the presence of a first etherification catalyst whereby said alkyl alcohol reacts with said iso-olefins to form alkyl-tert-alkyl ethers so as to provide an intermediate feedstock containing said ethers and unreacted iso-olefins and alkyl alcohol;
feeding said intermediate feedstock to a catalytic distillation column having a second etherification catalyst defining a catalytic zone;
mixing additional alkyl alcohol to said intermediate feedstock upstream of said catalytic zone wherein said step of feeding said intermediate feedstock and said mixing steps are carried out so as to provide a molar ratio of total alkyl alcohol to said unreacted iso-olefins of between about 2.5 and 6.0 so as to form azeotropes of said alkyl alcohol with said unreacted iso-olefins without forming azeotropes of said alkyl alcohol with said ethers whereby said azeotropes of said alkyl alcohol with said unreacted iso-olefins flow to said catalytic zone and said ethers are removed as bottoms from said catalytic distillation column wherein said catalytic zone is substantially free of said ethers and wherein said unreacted iso-olefins in said catalytic zone react with said additional alkyl alcohol in said catalytic zone to form additional alkyl-tert-alkyl ethers which are removed as bottoms.

2. A process according to claim 1, wherein said step of feeding said intermediate feedstock and said mixing step are carried out so as to provide a methanol content in said catalytic zone based on weight of liquid phase in said zone of between about 15% and about 50%.

3. A process according to claim 1, wherein said catalytic distillation column is operated at a pressure of between about 1.5 barg and about 4.0 barg.

4. A process according to claim 1, wherein said catalytic distillation column is operated at a reboiler temperature of between about 120° C. and about 170° C.

5. A process according to claim 1, wherein said catalytic distillation column is operated at a reflux ratio by volume of between about 0.7 and about 2.5.

6. A process according to claim 1, wherein said catalytic distillation column is operated at a temperature in said catalytic zone of between about 60° C. and about 90° C.

7. A process according to claim 1, wherein said alkyl alcohol is methanol.

8. A process according to claim 1, wherein said iso-olefins comprise iso-C5 and iso-C6, and wherein said ethers comprise tert-amyl-methyl-ether (TAME) and methyl-tert-hexyl-ether (MTHE).

9. A process according to claim 1, wherein said first etherification catalyst comprises an acidic ion exchange resin.

10. A process according to claim 9, wherein said reactor zone comprises a plurality of reaction zones including a first zone and at least one additional zone, each containing an etherification catalyst, and wherein said etherification catalyst in said first zone is doped with a noble metal.

11. A process according to claim 1, wherein said step of mixing said feedstock with said alkyl alcohol provides said reaction feedstock to said reactor zone having a molar ratio of alkyl alcohol to iso-olefins of between about 1.05 and about 1.6.

12. A process according to claim 1, wherein said second etherification catalyst comprises an acidic macroporous resin.

13. A process according to claim 1, wherein said feedstock is a C5/C6 cut from a light catalytic cracking naphtha (LCCN).

14. A process according to claim 1, wherein said catalytic distillation column provides a conversion of said unreacted C5 iso-olefins to tert-amyl-methyl-ether (TAME) of at least about 10% (wt.).

15. A process according to claim 1, wherein said catalytic distillation column provides a conversion of said C6 iso-olefins to methyl-tert-hexyl-ether (MTHE) of at least about 20% (wt.).

16. A process according to claim 1, wherein said feedstock contains iso-C5 and iso-C6, and wherein said reactor zone and said catalytic distillation column provide a total conversion of said iso-C5 to tert-amyl-methyl-ether (TAME) of at least about 70% (wt.) and a total conversion of said iso-C6 to methyl-tert-hexyl-ether (MTHE) of at least about 55% (wt.).

* * * * *